(12) United States Patent
Yang

(10) Patent No.: US 8,591,429 B2
(45) Date of Patent: Nov. 26, 2013

(54) PHYSIOLOGICAL PARAMETER ESTIMATION USING PHASE-LOCKED LOOP

(75) Inventor: Te-Chung Isaac Yang, Aliso Viejo, CA (US)

(73) Assignee: Sharp Laboratories of America, Inc., Camas, WA (US)

( * ) Notice: Subject to any disclaimer, the term of this patent is extended or adjusted under 35 U.S.C. 154(b) by 29 days.

(21) Appl. No.: 13/358,772

(22) Filed: Jan. 26, 2012

(65) Prior Publication Data

US 2013/0197382 A1 Aug. 1, 2013

(51) Int. Cl.
*A61B 5/02* (2006.01)

(52) U.S. Cl.
USPC ............................. 600/528; 600/508; 600/586

(58) Field of Classification Search
USPC ........................................ 600/508, 528, 586
See application file for complete search history.

(56) References Cited

U.S. PATENT DOCUMENTS

| | | | | |
|---|---|---|---|---|
| 4,122,427 A * | 10/1978 | Karsh | ............................... | 367/89 |
| 4,202,340 A | 5/1980 | Heilman et al. | | |
| 4,494,553 A * | 1/1985 | Sciarra et al. | ................. | 600/534 |
| 4,519,396 A * | 5/1985 | Epstein et al. | ................. | 600/511 |
| 4,822,162 A | 4/1989 | Richardson et al. | | |
| 5,254,958 A | 10/1993 | Flach et al. | | |
| 5,260,812 A | 11/1993 | McNeilly et al. | | |
| RE34,663 E * | 7/1994 | Seale | ............................. | 600/587 |
| 5,539,357 A * | 7/1996 | Rumreich | ........................ | 331/17 |
| 5,680,868 A * | 10/1997 | Kahn et al. | ..................... | 600/494 |
| 5,685,317 A * | 11/1997 | Sjostrom | ........................ | 600/528 |
| 5,749,831 A * | 5/1998 | Baker | ............................. | 600/301 |
| 5,792,073 A * | 8/1998 | Keefe | ............................. | 600/559 |
| 6,053,872 A * | 4/2000 | Mohler | ............................ | 600/485 |
| 6,150,941 A * | 11/2000 | Geiger et al. | .............. | 340/573.1 |
| 6,426,977 B1 * | 7/2002 | Lee et al. | ........................ | 375/259 |
| 6,520,918 B1 * | 2/2003 | Stergiopoulos et al. | ....... | 600/490 |
| 6,543,272 B1 * | 4/2003 | Vitek | ............................... | 73/1.83 |
| 7,218,665 B2 * | 5/2007 | McElwain | ..................... | 375/143 |
| 8,086,304 B2 * | 12/2011 | Brockway et al. | ............. | 600/515 |
| 2002/0143259 A1 * | 10/2002 | Stergiopoulos et al. | ....... | 600/490 |
| 2003/0139674 A1 * | 7/2003 | Stergiopoulos et al. | ....... | 600/490 |
| 2005/0015009 A1 * | 1/2005 | Mourad et al. | ................. | 600/438 |
| 2005/0249667 A1 * | 11/2005 | Tuszynski et al. | .............. | 424/9.3 |
| 2006/0025686 A1 * | 2/2006 | Ueno et al. | ..................... | 600/443 |
| 2007/0032733 A1 * | 2/2007 | Burton | ........................... | 600/509 |
| 2008/0188763 A1 * | 8/2008 | John et al. | ...................... | 600/516 |
| 2009/0149751 A1 * | 6/2009 | Mourad et al. | ................. | 600/438 |
| 2010/0292568 A1 * | 11/2010 | Droitcour et al. | .............. | 600/425 |
| 2010/0324612 A1 * | 12/2010 | Matos | ................................ | 607/4 |
| 2011/0125063 A1 * | 5/2011 | Shalon et al. | .................. | 600/590 |
| 2011/0213271 A1 * | 9/2011 | Telfort et al. | .................. | 600/586 |
| 2011/0213272 A1 * | 9/2011 | Telfort et al. | .................. | 600/586 |
| 2011/0213273 A1 * | 9/2011 | Telfort et al. | .................. | 600/586 |
| 2011/0213274 A1 * | 9/2011 | Telfort et al. | .................. | 600/586 |

* cited by examiner

*Primary Examiner* — George Manuel
*Assistant Examiner* — Christopher A Flory
(74) *Attorney, Agent, or Firm* — Scot A. Reader

(57) ABSTRACT

A method and device for physiological parameter estimation, such as heart rate estimation, use a phase-locked loop to dynamically track a dominant frequency of an acoustic signal within a frequency band for the physiological parameter and estimate the physiological parameter using the dominant frequency. Because the phase-locked loop starts searching for the current dominant frequency near the most recently identified dominant frequency, the method and device rapidly incorporate slow changes in the dominant frequency that likely reflect real changes in the monitored physiological parameter while being slow to incorporate rapid changes in the dominant frequency that are likely caused by large noise. The hysteresis in phase-locked loop tracking allows the method and device to avoid physiological parameter estimation error induced by short-term large noise and quickly reacquire the dominant frequency once short-term large noise abates.

18 Claims, 2 Drawing Sheets

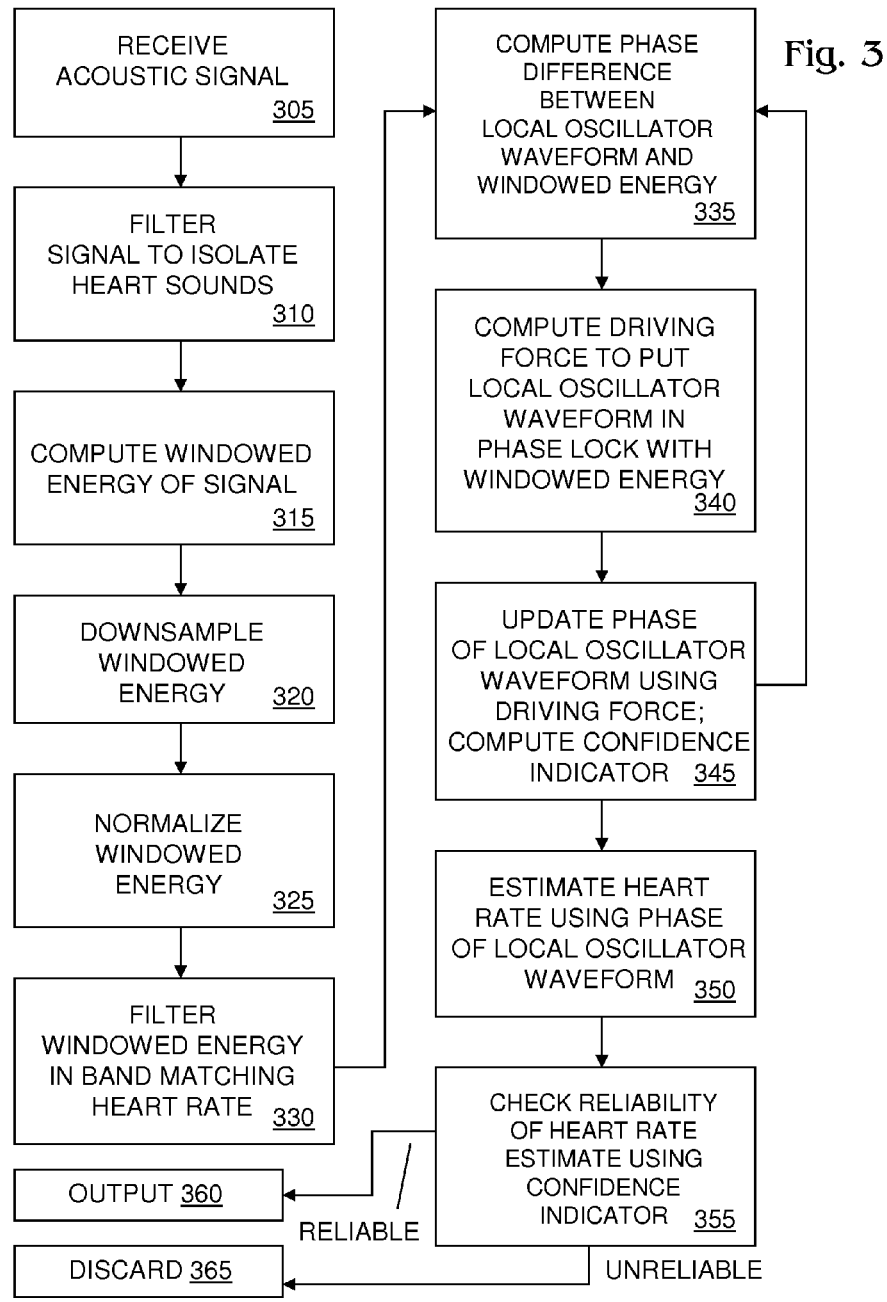

PHYSIOLOGICAL PARAMETER ESTIMATION USING PHASE-LOCKED LOOP

BACKGROUND OF THE INVENTION

The present invention relates to acoustic physiological monitoring and, more particularly, physiological parameter estimation in acoustic physiological monitoring.

Real-time physiological monitoring can be helpful in maintaining the health of people as they go about their daily lives. For example, real-time physiological monitoring can be used to rapidly detect heart or respiratory ailments.

Real-time physiological monitoring often invokes the body sound method, which is sometimes called auscultation. In the body sound method, an acoustic transducer mounted on the body of the person captures and acquires an acoustic signal recording body sounds, such as heart or respiration sounds. Once the acoustic signal has been generated, a heartbeat or respiration sequence may be identified in the acoustic signal and heart or respiration rate may be estimated. Health status information based on the heart or respiration rate estimate may then be outputted locally to the monitored person or remotely to a clinician.

Many known real-time physiological monitoring systems analyze an acoustic signal in the time or frequency domain to estimate heart or respiration rate. For example, a time domain technique for estimating heart rate generally uses autocorrelation to identify the fundamental periodicity in the acoustic signal within the frequency band for heart sounds by analyzing recurring energy peaks. The recurring energy peaks are recognized as heartbeats and heart rate is estimated using the distance between adjacent energy peaks. A frequency domain technique for estimating heart rate generally evaluates spectral density of different frequencies within the frequency band for heart sounds and identifies the most significant frequency as the heartbeat frequency, from which heart rate is estimated.

Both of these conventional approaches to estimating heart rate work well when the signal-to-noise ratio is sufficiently high, but are prone to problems in the presence of large noise. An acoustic signal that records body sounds can be disrupted by several types of large noise, including short-term, high amplitude noise introduced by impulse events such as talking, coughing or sneezing. Large noise can mask the heartbeat, resulting in erroneous heart rate estimation and outputting of erroneous health status information. In turn, reliance on erroneous health status information can have serious adverse consequences on the health of the monitored person. For example, such information can lead the person or his or her clinician to improperly diagnose health status and cause the person to undergo treatment that is not medically indicated or forego treatment that is medically indicated.

Some known approaches attempt to combat noise-induced heart rate estimation error by trying to remove large noise from the acoustic signal, such as by using a reference microphone to measure environmental noise and attempting to cancel the noise through differentiation. Other known approaches attempt to combat such error by isolating noisy portions of the acoustic signal and excluding them when estimating heart rate. However, these noise handling approaches add substantial complexity to the physiological monitoring system and at best only offer piecemeal solutions.

SUMMARY OF THE INVENTION

The present invention provides a method and device for physiological parameter estimation, such as heart rate estimation, that use a phase-locked loop to dynamically track a dominant frequency of an acoustic signal within a frequency band for the physiological parameter and estimate the physiological parameter using the dominant frequency. Because the phase-locked loop starts searching for the current dominant frequency near the most recently identified dominant frequency, the method and device rapidly incorporate slow changes in the dominant frequency that likely reflect real changes in the monitored physiological parameter while being slow to incorporate rapid changes in the dominant frequency that are likely caused by large noise. The hysteresis in the phase-locked loop allows the method and device to avoid physiological parameter estimation error induced by short-term large noise and quickly reacquire the dominant frequency once short-term large noise abates.

In one aspect of the invention, a physiological monitoring device comprises a sound capture system configured to generate an acoustic signal recording body sounds; an acoustic signal processing system configured to receive from the sound capture system the signal, compute a windowed energy of the signal, lock a phase of a local oscillator waveform to a phase of the windowed energy using a phase-locked loop and compute an estimate of a physiological parameter based at least in part on a frequency of the local oscillator waveform while in locked phase with the windowed energy; and a physiological data output system configured to output information based at least in part on the physiological parameter estimate.

In some embodiments, the phase-locked loop computes a phase difference between the local oscillator waveform and the windowed energy, computes a driving force required to lock the phase of the local oscillator waveform to the phase of the windowed energy using the phase difference and updates the phase of the local oscillator waveform using the driving force.

In some embodiments, the phase-locked loop computes the phase difference as a product of the local oscillator waveform and the windowed energy.

In some embodiments, the phase-locked loop computes a phase lock confidence indicator based at least in part on a time-averaged product of the local oscillator waveform and the windowed energy at a ninety degree phase shift.

In some embodiments, the acoustic signal processing system is configured to compare the confidence indicator with a predetermined reliability threshold.

In some embodiments, the acoustic signal processing system is configured to filter the signal to isolate sounds within a frequency band for body sounds from which the physiological parameter is computed prior to computing the windowed energy.

In some embodiments, the acoustic signal processing system is configured to downsample the windowed energy prior to locking the phase.

In some embodiments, the acoustic signal processing system is configured to normalize the windowed energy in a range between −1 and +1 prior to locking the phase.

In some embodiments, the acoustic signal processing system is configured to filter the windowed energy in a frequency band for the physiological parameter prior to locking the phase.

In some embodiments, the physiological parameter estimate is a heart rate estimate.

In another aspect of the invention, a method for estimating a physiological parameter comprises the steps of generating by a physiological monitoring system an acoustic signal recording body sounds; computing by the system a windowed energy of the signal; locking by the system a phase of a local oscillator waveform to a phase of the windowed energy using a phase-locked loop; computing by the system an estimate of a physiological parameter based at least in part on a frequency of the local oscillator waveform while in locked phase with the windowed energy; and outputting by the system information based at least in part on the physiological parameter estimate.

These and other aspects of the invention will be better understood by reference to the following detailed description taken in conjunction with the drawings that are briefly described below. Of course, the invention is defined by the appended claims.

BRIEF DESCRIPTION OF THE DRAWINGS

FIG. 3 shows a heart rate estimating method in some embodiments of the invention.

DETAILED DESCRIPTION OF A PREFERRED EMBODIMENT

Figure 1:
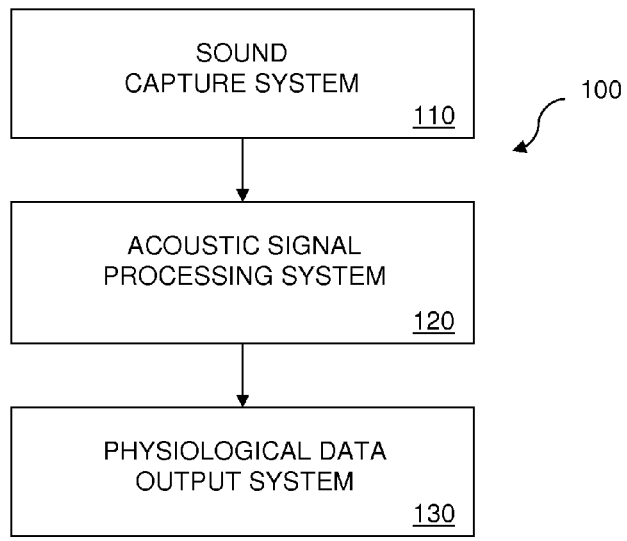
FIG. 1 shows an acoustic physiological monitoring device in some embodiments of the invention.

FIG. 1 shows an acoustic physiological monitoring device 100 in some embodiments of the invention. Monitoring device 100 includes a sound capture system 110, an acoustic signal processing system 120 and a physiological data output system 130, which are communicatively coupled in series.

Capture system 110 continually detects body sounds, such as lung and heart sounds, at a detection point, such as the trachea, chest or back of a person being monitored, and continually transmits an acoustic signal recording the detected body sounds to processing system 120. Capture system 110 may include, for example, a sound transducer positioned on the body of a human subjects that detects body sounds, as well as amplifiers, filters an analog/digital converter and/or automatic gain control that generate an acoustic signal embodying the detected body sounds. The body sounds may include, for example, heart sounds, lung sounds and speech.

Processing system 120, under control of a processor executing software instructions, continually processes the acoustic signal and generates estimates of one or more physiological parameters for the subject being monitored using the acoustic signal. Monitored physiological parameters include heart rate. In some embodiments, monitored physiological parameters additionally include one or more respiration parameters, such as respiration rate.

In some embodiments, processing system 120 performs at least some of the processing operations described herein in custom logic rather than software.

Output system 130 has a display screen for displaying physiological information determined using physiological parameter estimates received from processing system 120. In some embodiments, output system 130, in addition to a display screen, has an interface to an internal or external data management system that stores physiological information determined using physiological parameter estimates received from processing system 120 and/or an interface that transmits such information to a remote monitoring device, such as a monitoring device at a clinician facility. Physiological information outputted by output system 130 may include physiological parameter estimates received from processing system 120 and/or information derived from physiological parameter estimates, such as a numerical score or color-coded indicator of present health status.

In some embodiments, capture system 110, processing system 120 and output system 130 are part of a portable ambulatory monitoring device that monitors a person's physiological well being in real-time as the person performs daily activities. In other embodiments, capture system 110, processing system 120 and output system 130 may be part of a stationary device or separate devices that are remotely coupled via wired or wireless communication links.

Figure 2:
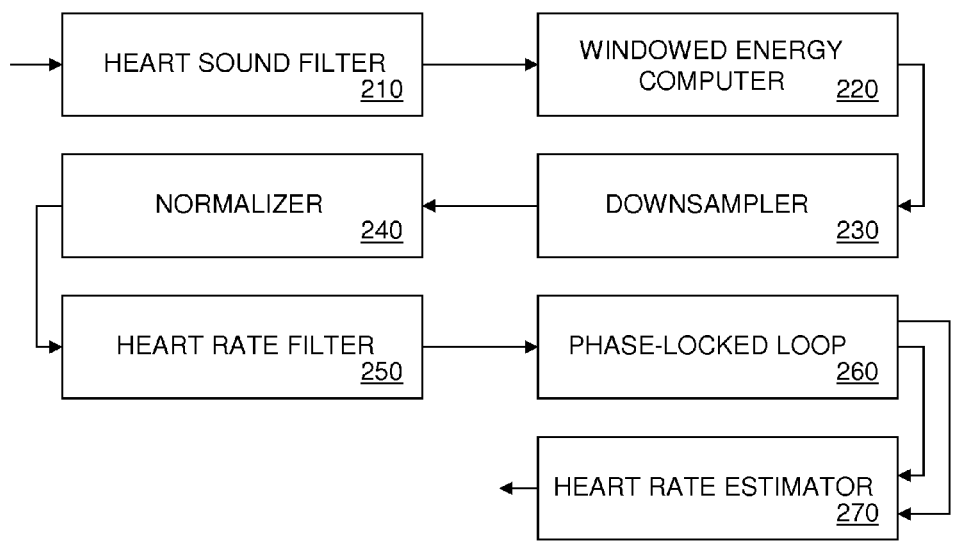
FIG. 2 shows an acoustic signal processing system in some embodiments of the invention.

FIG. 2 shows processing system 120 to include a heart sound filter 210, a windowed energy computer 220, a downsampler 230, a normalizer 240, a heart rate filter 250, a phase-locked loop 260 and a heart rate estimator 270, which are communicatively coupled in series. Normalizer 240 and heart rate filter 250 are operative in the sequence before phase-locked loop 260 to convert windowed energy from heart sounds into a signal similar to a sinusoidal waveform having an amplitude range-bounded between −1 to +1, as expected by phase-locked loop 260. These system components will now be further described in connection with the heart rate estimating method of FIG. 3.

In the method, heart sound filter 210 receives from capture system 110 an acoustic signal recording detected body sounds (305) and filters the signal to isolate heart sounds (310). Heart sound filter 210 is a bandpass filter having a range where heart sounds are normally concentrated, such as 25 Hz to 75 Hz. As such the signal after application of heart sound filter 210 retains heart sounds while removing unwanted body sounds and noise. Heart sound filter 210 outputs the filtered signal to windowed energy computer 220.

Windowed energy computer 220 computes the total energy of the filtered signal inside small time windows to generate windowed energy values (315). By way of example, windowed energy values may be computed using a sliding window that is ten samples in length. Windowed energy values are outputted to downsampler 230.

Downsampler 230 downsamples the windowed energy values to reduce computational and data storage requirements (320). By way of example, an acoustic signal having a sampling rate of 3200 Hz may be downsampled by a factor of 10 to 320 Hz where the physiological parameter of interest is heart rate. As a typical heart rate is between 48 and 200 beats per minute, body sounds of interest are well preserved in the downsampled windowed energy values. Downsampler 230 outputs the windowed energy values to normalizer 240.

Normalizer 240 range-bounds the windowed energy values between −1 and +1 (325). Normalizer 240 first applies a high-pass filter that removes the DC component of energy from the current windowed energy value. After application of the high-pass filter, a windowed energy value may be positive or negative. Normalizer 240 then normalizes the current windowed energy value by dividing the current value by a global maximum (GM) that is computed using previous windowed energy values. In this normalization process, normalizer 240 first identifies a maximum value from a number of immediately preceding windowed energy values, excepting the current value. This maximum value is deemed the local maximum (LM). By way of example, the number of immediately preceding values used to determine the local maximum may include all windowed energy values from the previous two seconds. Next, normalizer 240 determines whether the local maximum is greater than or less than the global maximum. Next, normalizer 240 updates the global maximum according to the formula $$GM_N = LM*p + GM_{N-1}*(1-p)$$

where p is selected to be between 0.5 and 1 if the local maximum is greater than the global maximum and p is selected to be between 0 and 0.5 if the global maximum is greater than the local maximum. In some embodiments, p is assigned a value of 0.6 where the local maximum is greater than the global maximum and 0.3 where the global maximum is greater than the local maximum. Finally, normalizer 240 updates the current value by dividing the current value by the global maximum. In some embodiments, normalizer 240 proceeds to apply a clipping function to the current value to ensure that the value is between −1 and +1. Normalizer 240 outputs the normalized windowed energy values to heart rate filter 250.

Heart rate filter 250 filters the windowed energy values to remove sounds outside of the normal heart rate band (330). Heart sound filter 210 is a bandpass filter having a range that matches typical human heart rates, such as 48 to 200 beats per minute. Heart rate filter 250 outputs the filtered windowed energy values to phase-locked loop 260. At this point, the windowed energy values form a signal that resembles a sinusoidal waveform having an amplitude that is range-bounded between −1 to +1 and is ready for processing by phase-locked loop 260.

Phase-locked loop 260 first estimates a phase difference between the windowed energy values and a local oscillator waveform (335) as the product (P) of the windowed energy values and a local oscillator waveform. The local oscillator waveform is a pure sinusoidal waveform that initially operates a predetermined free-run frequency.

Phase-locked loop 260 next estimates a driving force (DF) required to put the local oscillator waveform in locked phase with the windowed energy values (340). The driving force estimate is computed according to the formula $$DF_N = DF_{N-1} + Ki*P_N + Kp*P_N - Kp*P_{N-1}$$

where Ki and Kp are constants that represent characteristics of a low pass filter applied to the product. In some embodiments, Ki and Kp are determined by the formulas $$Ki = (0.5*\pi/f)^2;\ Kp = [\pi/f]\text{sqrt}(2)] - Ki$$

where f is the sampling frequency of the windowed energy after downsampling. For the initial driving force estimate, $DF_{N-1}$ and $P_{N-1}$ may be assigned predetermined values.

Phase-locked loop 260 next updates the phase (PH) of local oscillator waveform according to the formula $$PH_N = PH_{N-1} + DF_N$$

and computes a confidence indicator as a time-averaged product of the local oscillator waveform and the windowed energy values at a ninety degree phase shift (345). Phase-locked loop 260 transmits the frequency of the local oscillator waveform and confidence indicator to heart rate estimator 270 and loops-back to Step 335 whereupon an updated driving force estimate is computed and compared with the phase lock threshold.

Heart rate estimator 270 applies the frequency of the local oscillator waveform (F) received from phase-locked loop 260 and the phase of local oscillator waveform over a short time period to estimate the heart rate (HR) according to the formula $$HR = F + (PH_N - PH_{N-K+1})/D$$

where D is the duration of the short time period multiplied by $2\pi$ and K is the number of samples inside the duration (350). Heart rate estimator 270 then converts the heart rate estimate into beats per minute by multiplying by 60.

Heart rate estimator 270 then checks the reliability of the heart rate estimate by comparing the confidence indicator received from phase-locked loop 260 with a predetermined reliability threshold (355). In this regard, if the confidence indicator is above the reliability threshold, the heart rate estimate is considered reliable and heart rate estimator 270 outputs the heart rate estimate to output system 130 (360), which outputs physiological information that may include the heart rate estimate itself and/or information derived from the estimate. On the other hand, if the confidence indicator is below the reliability threshold, the heart rate estimate is considered unreliable and heart rate estimator 270 discards the heart rate estimate (365). In some embodiments, the reliability threshold (RT) is set according to the formula $$RT = f*K/4$$

where f is the sampling frequency of the windowed energy after downsampling and K is the number of samples inside the duration.

It will be appreciated by those of ordinary skill in the art that the invention can be embodied in other specific forms without departing from the spirit or essential character hereof. For example, while a method for estimating heart rate has been described in detail, the invention may be applied in estimation of other physiological parameters, such as respiration rate. The present description is considered in all respects to be illustrative and not restrictive. The scope of the invention is indicated by the appended claims, and all changes that come with in the meaning and range of equivalents thereof are intended to be embraced therein.

What is claimed is:

1. A physiological monitoring device, comprising:
    a sound capture system configured to generate an acoustic signal recording heart sounds;
    an acoustic signal processing system configured to receive from the sound capture system the signal, compute a windowed energy of the signal, invoke a phase-locked loop to compute a phase difference between a phase of a local oscillator waveform and a phase of the windowed energy and update the phase of the local oscillator waveform using the phase difference, and compute an estimate of heart rate using as algorithmic input a frequency of the local oscillator waveform; and
    a physiological data output system configured to output information based at least in part on the heart rate estimate.

2. The device of claim 1, wherein the phase-locked loop computes a driving force required to lock the phase of the local oscillator waveform to the phase of the windowed energy using the phase difference and updates the phase of the local oscillator waveform using the driving force.

3. The device of claim 2, wherein the phase-locked loop computes the phase difference as a product of the local oscillator waveform and the windowed energy.

4. The device of claim 1, wherein the phase-locked loop computes a phase lock confidence indicator based at least in part on a time-averaged product of the local oscillator waveform and the windowed energy at a ninety degree phase shift.

5. The device of claim 4, wherein the acoustic signal processing system is configured to compare the confidence indicator with a predetermined reliability threshold.

6. The device of claim 1, wherein the acoustic signal processing system is configured to filter the signal to isolate the heart sounds prior to computing the windowed energy.

7. The device of claim 1, wherein the acoustic signal processing system is configured to downsample the windowed energy prior to locking the phase.

8. The device of claim 1, wherein the acoustic signal processing system is configured to normalize the windowed energy in a range between −1 and +1 prior to locking the phase.

9. The device of claim 1, wherein the acoustic signal processing system is configured to filter the windowed energy in a frequency band for heart rate prior to locking the phase.

10. A method for estimating a physiological parameter, comprising the steps of:
   generating by a physiological monitoring system an acoustic signal recording heart sounds;
   computing by the system a windowed energy of the signal;
   invoking by the system a phase-locked loop to compute a phase difference between a phase of a local oscillator waveform and a phase of the windowed energy and update the phase of the local oscillator waveform using the phase difference;
   computing by the system an estimate of heart rate using as algorithmic input a frequency of the local oscillator waveform; and
   outputting by the system information based at least in part on the heart rate estimate.

11. The method of claim 10, wherein the invoking step comprises the substeps of:
   computing a driving force required to lock the phase of the local oscillator waveform to the phase of the windowed energy using the phase difference; and
   updating the phase of the local oscillator waveform using the driving force.

12. The method of claim 11, wherein the phase difference is computed as a product of the local oscillator waveform and the windowed energy.

13. The method of claim 10, further comprising the step of computing by the system a phase lock confidence indicator based at least in part on a time-averaged product of the local oscillator waveform and the windowed energy at a ninety degree phase shift.

14. The method of claim 13, further comprising the step of comparing by the system the confidence indicator with a predetermined reliability threshold.

15. The method claim 10, further comprising the step of filtering by the system the signal to isolate the heart sounds.

16. The method of claim 10, further comprising the step of downsampling by the system the windowed energy.

17. The method claim 10, further comprising the step of normalizing by the system the windowed energy in a range between −1 and +1.

18. The method of claim 10, further comprising the step of filtering by the system the windowed energy in a frequency band for heart rate.

* * * * *